United States Patent [19]

Weber et al.

[11] 4,097,334
[45] Jun. 27, 1978

[54] PROCESS FOR THE PREPARATION OF ANDROSTANE-3,17-DIONE DERIVATIVES

[75] Inventors: Alfred Weber; Mario Kennecke; Rudolf Müeller; Ulrich Eder; Rudolf Wiechert, all of Berlin, Germany

[73] Assignee: Schering Aktiengesellschaft, Berlin & Bergkamen, Germany

[21] Appl. No.: 751,672

[22] Filed: Dec. 17, 1976

[30] Foreign Application Priority Data

Dec. 19, 1975 Germany .............................. 2558089

[51] Int. Cl.² .................................................. C07B 29/00
[52] U.S. Cl. ..................................................... 195/51 G
[58] Field of Search ....................................... 195/51 G

[56] References Cited

U.S. PATENT DOCUMENTS

| | | | |
|---|---|---|---|
| 3,388,042 | 6/1968 | Arima et al. | 195/51 G |
| 3,684,656 | 8/1972 | Waard | 195/51 G |
| 3,759,791 | 9/1973 | Marsheck et al. | 195/51 G |

*Primary Examiner*—Alvin E. Tanenholtz
*Attorney, Agent, or Firm*—Millen & White

[57] ABSTRACT

A process for the preparation of androstane-3,17-dione compounds of the formula

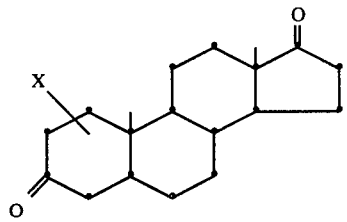

wherein X is 1,2-methylene or 1- or 2-methyl, comprises fermenting a sterol of the formula

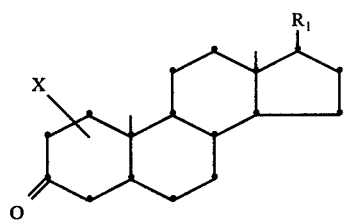

wherein X is as above and $R_1$ is the hydrocarbon residue of 8–10 carbon atoms, of a sterol, with a microorganism culture capable of effecting the side chain degradation of sterols.

10 Claims, No Drawings

PROCESS FOR THE PREPARATION OF ANDROSTANE-3,17-DIONE DERIVATIVES

BACKGROUND OF THE INVENTION

Numerous microorganisms, for example, of the genera Arthrobacter, Brevibacterium, Microbacterium, Protaminobacter, Bacillus, Norcardia, or Streptomyces, especially Mycobacterium, are capable of degrading zoosterols and phytosterols to carbon dioxide and water. During this degradation, 4-androstene-3,17-dione and 1,4-androstadiene-3,17-dione are formed as intermediates.

It is possible, by using inhibiting additives or mutated microorganisms to control degradation of the sterols to prevent further degradation of the thus-formed 4-androstene-3,17-dione or 1,4-androstadiene-3,17-dione. See DOS's (German Unexamined Laid-Open Application) 1,543,269 and 1,593,327, and U.S. Pat. No. 3,684,657.

SUMMARY OF THE INVENTION

This invention relates to a process for the preparation of an androstane-3,17-dione compound of Formula I

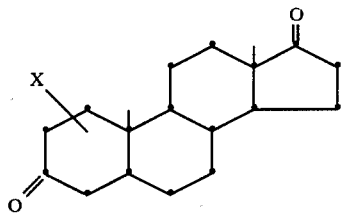

wherein X is 1,2-methylene or 1- or 2-methyl, comprising fermenting a sterol of Formula II

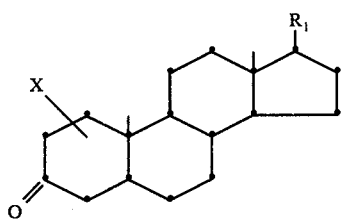

wherein X is as above and $R_1$ is a saturated or unsaturated hydrocarbon sterol side chain of 8-10 carbon atoms with a microorganism culture capable of degrading the sterol side chain.

DETAILED DESCRIPTION

A sterol hydrocarbon residue $R_1$ of 8-10 carbon atoms is an unsaturated or hydrogenated side chain of a naturally occurring zoosterol or phytosterol, e.g., cholesterol, stigmasterol, campesterol, brassicasterol, or the sitosterols.

Sterol compounds of Formula II are, for example, compounds which of Formula II a

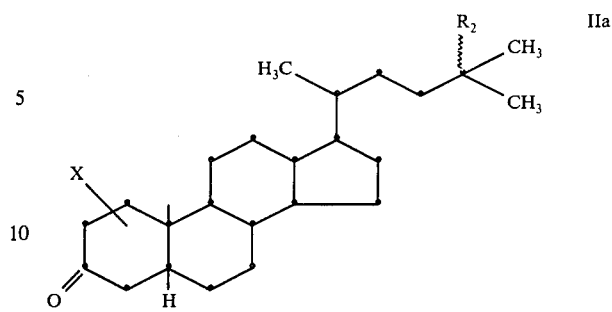

wherein X is as above and $R_2$ is hydrogen, methyl or ethyl.

Suitable starting materials for the process of this invention are, for example, sterols wherein X is 1α-methyl, 1β-methyl, 1α,2α-methylene, or 1β,2β-methylene. Examples of suitable starting compounds are:
  1α-methyl-5α-cholestan-3-one,
  1β-methyl-5α-cholestan-3-one,
  1α,2α-methylene-5α-cholestan-3-one,
  1α-methyl-5α-stigmastan-3-one,
  1α,2α-methylene-5α-stigmasten-3-one, or the corresponding sitosterol derivatives.

Although different starting compounds are used and the reaction can be conducted in the absence of inhibitors, the process of the invention is accomplished under the same fermentation conditions utilized in conventional microbiological side chain degradation reactions of sterols.

The fermentation is conducted using microorganism cultures customarily employed for the side chain degradation of sterols. Suitable cultures are, for example, those of the genera Arthrobacter, Brevibacterium, Microbacterium, Protaminobacter, Streptomyces. Those of the genus Mycobacterium are preferred.

Examples of suitable microorganisms are: *Microbacterium lactum* IAM-1640, *Protaminobacter alboflavus* IAM-1040, Bacillus roseus IAM-1257, *Bacillus sphaericus* ATCC-7055, *Norcardia gardneri* IAM-105, *Morcardia minima* IAM-374, *Norcardia corallina* IFO-3338, *Streptomyces rubescens* IAM-74 or especially the microorganisms *Mycobacterium avium* IFO-3082, *Mycobacterium phlei* IFO-3158, *Mycobacterium phlei* (Institute of Health, Budapest No. 29), *Mycobacterium phlei* ATCC-354, *Mycobacterium smegmatis* IFO-3084, *Mycobacterium smegmatis* ATCC-20, *Mycobacterium smegmatis* (Institute of Health, Budapest No. 27), *Mycobacterium smegmatis* ATCC-19979, *Mycobacterium fortuitum* CBS-49566, Mycobacterium spec. NRRL-B-3805, and Mycobacterium spec. NRRL-B-3683. Mycobacterium spec. NRRL-B-3805 is most preferred.

Submerged cultures are grown under conditions customarily employed for these microorganisms, using a suitable nutrient medium with aeration. Then, the substrate, dissolved in a suitable solvent or preferably in emulsified form, is added to the culture and the fermentation is conducted until maximum substrate conversion has been attained.

Suitable solvents for the substrate are, for example, methanol, ethanol, glycol monomethyl ether, dimethylformamide, or dimethyl sulfoxide. The substrate can be emulsified, for example, by adding micronized substrate or substrate dissolved in a water-miscible solvent, e.g., methanol, ethanol, acetone, glycol monomethyl ether, dimethylformamide, or dimethyl sulfoxide, through nozzles under strongly turbulent conditions, to, preferably decalcified, water containing the customary emulsifying agents. Suitable emulsifying agents include non-ionic emulsifiers, for example, ethylene oxide adducts or fatty acid esters of polyglycols. Examples of suitable emulsifiers are surfactants commercially available, as "Tegin", "Tween", and "Span".

The optimum substrate concentration, time of substrate addition, and duration of fermentation depend on the structure of the substrate employed and on the type of the microorganism utilized. These variables must be determined in each individual case by means of preliminary experiments well-known to those skilled in the art.

It is surprising to those skilled in the art that, under otherwise conventional conditions, the side chains of sterols of Formula II are degraded, because it is known that side chain degradation of sterols is effected by a very complex fermentation system. It is unexpected that the enzymes taking part in the side chain degradation of natural steroids also cause side chain degradation of the sterol derivatives of Formula II, which do not occur in nature. Moreover, it could not be foreseen that enzyme systems effecting degradation of 1,4-androstadiene-3,17-dione and of 4-androstene-3,17-dione are incapable of further degrading androstane-3,17-dione derivatives of Formula I.

Androstane-3,17-dione compounds of Formula I which can be produced by the process of the present invention are valuable intermediates for the synthesis of pharmacologically active steroids, e.g., 17β-hydroxy-1α-methyl-5α-androstan-3-one, 17β-hydroxy-1-methyl-5α-androst-1en-3-one, 2α-methyl-17β-propionyloxy-5α-androstan-3-one and 1,2α-methylene-17α-hydroxy-4,6-pregnadiene3,20-dione. The 17-keto group of the androstane-3,17-dione compounds can be reduced optionally after ketalizing the 3-oxo group. Also, the 17-keto group can be reacted with an organometallic compound of the formula MeR$_4$ wherein R$_4$ is alkyl, alkenyl or alkinyl of up to 4 carbon atoms and Me is an alkali metal atom or a magnesium halide residue. After cleaving the ketal group, which may be present, 17β-hydroxyandrostan-3-one compounds of Formula III

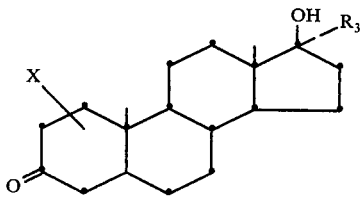

wherein X is as above and R$_3$ is R$_4$ or hydrogen, are obtained.

When R$_3$ is alkyl, alkenyl or alkinyl, it is preferably methyl, ethyl, vinyl or ethynyl.

The 17-keto group of androstane-3,17-dione compoudns of Formula I is reduced by methods well-known to those skilled in the art. See, for example, John Fried: Organic Reactions in Steroid Chemistry, van Nostrand Reinhold Comp., New York, etc. (1972) I : 61 et seq. These compounds can be reacted, for example, after ketalization, with sodium borohydride or lithium aluminum hydride, to obtain, after cleaving the ketals, the corresponding 17β-hydroxyandrostan-3-one derivatives of Formula III which possess an anabolic and/or androgenic activity.

Methods for alkylating the 17-keto group are likewise known. See, for example, John Fried: Organic Reactions in Steroid Chemistry, van Nostrand Reinhold Comp., New York, etc. (1972) 2 : 53 et seq. Androstane-3,17-dione derivatives of Formula I can be reacted, optionally after ketalizing the 3-oxo group, with alkyl magnesium halides, vinyllithium, or alkali metal acetylides. After removing the optionally present ketal group, the 17αR-17β-hydroxyandrostan-3-one derivatives of Formula III are obtained. These compounds are pharmacologically active substances or intermediates for the preparation of pharmacologically active steroids, e.g., 17β-hydroxy-17α-methyl-5α-androstan-3,2 c-pyrazole.

The sterols of Formula II utilized as starting compounds can be produced from the corresponding naturallyoccurring sterols by means conventionally utilized for introducing substituents at the 1- and/or 2-positions of steroids. References to these conversions are: John Fried and John A. Edwards: Organic Reactions in Steroid Chemistry; van Nostrand Reinhold Comp., New York, 1972.

The following references on fermentation processes describe techniques customary in the art: (G. S. Fonken and R. A. Johnson: Chemical Oxydations with Microorganism: Macel Dekker Inc., New York, 1972.

The following examples serve to explain the invention.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

(A) Examples Concerning the Microbiological Side Chain Degradation

EXAMPLE 1

A 2-liter Erlenmeyer flask containing 500 ml. of a sterile nutrient medium containing 1% yeast extract, 0.45% disodium hydrogen phosphate, 0.34% potassium dihydrogen phosphate, and 0.2% "Tween" 80, adjusted to pH 6.7, is inoculated with a suspension of a Mycobacterium spec. NRRL-B-3805 dry culture and shaken for three days at 30° C. at 190 r.p.m.

Twenty Erlenmeyer flasks, each containing 100 ml. of a sterile nutrient medium, containing 2.0% corn steep liquor, 0.3% diammonium hydrogen phosphate, and 0.25% "Tween" 80, adjusted to pH 6.5, are each inoculated with 5 ml. of the Mycobacterium spec. growth culture and shaken for 24 hours at 30° C. with 220 r.p.m.

Then, each culture is combined with 50 mg. of 1α-methyl-5α-cholestan-3-one dissolved in 1 ml. of dimethylformamide. The fermentation is continued for another 96 hours at 30° C.

The combined cultures are extracted with ethylene chloride. The extract is concentrated under vacuum. The residue is purified by chromatography over a silica gel column, thus obtaining after recrystallization from diisopropyl ether 0.5 g. of 1α-methyl-5α-androstane-3,17-dione, m.p. 140° C.

Preparation of the Starting Compound:

(a) 97 g. of 3β-hydroxy-5α-cholestane is made into a slurry with 1.5 l. of acetone, and under agitation, this slurry is combined within 20 minutes with 125 ml. of chromosulfuric acid, prepared from 267 g. of chromium (VI) oxide, 400 ml. of water, 230 ml. of concentrated sulfuric acid, and brought with water to 1000 ml. The mixture is then stirred for 1 hour at room temperature and stirred into ice water. The thus-precipitated product is filtered off. After drying, the product is recrystallized from diisopropyl ether, thus obtaining 72 g. of 5α-cholestan-3-one, m.p. 127.5°–128.5° C.

(b) 50 g. of 5α-cholestan-3-one is dissolved in 750 ml. of acetic acid and 5000 ml. of ether, combined with 1 ml. of hydrobromic acid in acetic acid (37% strength), and gradually added dropwise to a solution of 22 g. of bromine in 50 ml. of acetic acid. The mixture is agitated for another 30 minutes, diluted with methylene chloride, and washed in succession with water, sodium bicarbonate solution, and water. After drying and evaporation, 61.5 g. of crude 2α-bromo-5α-cholestan-3-one is obtained.

(c) 61.5 g. of crude 2α-bromo-5α-cholestan-3-one is agitated in 615 ml. of dimethylformamide with 29.3 g. of lithium carbonate and 34.5 g. of lithium bromide for 20 hours at 100° C. The mixture is then stirred into ice water. The thus-precipitated product is filtered off, washed thoroughly with water, and taken up in methylene chloride. The residue obtained after drying and evaporation is chromatographed on silica gel. Recrystallization from methanol yields 32 g. of 5α-cholest-1-en-3-one, m.p. 99.5°–100° C.

(d) 6.5 g. of magnesium filings are reacted in 160 ml. of absolute ether with 22 ml. of methyl iodide in 40 ml. of absolute ether to obtain methylmagnesium iodide. Under ice cooling, 405 ml. of absolute tetrahydrofuran is added thereto, and the ether is distilled off up to a boiling point of 62° C. Under agitation under nitrogen, 1.3 g. of copper (I) chloride is added to the Grignard solution, which had been cooled in an ice bath. 25 g. of 5α-cholest-1-en-3-one dissolved in 81 ml. of absolute tetrahydrofuran is added dropwise thereto. The mixture is then stirred for another 30 minutes with cooling, and the excess reagent is decomposed with saturated ammonium chloride solution. Thereafter, the mixture is diluted with ether. The aqueous phase is separated, and the ether phase is washed with saturated ammonium chloride solution and water. After drying and evaporation, the residue is chromatographed on silica gel and, after recrystallization from methanol, 16.5 g. of 1α-methyl-5α-cholestan-3-one is thus obtained, m.p. 132.5°–133° C.

EXAMPLE 2

Under the conditions of Example 1, 50 mg. portions of 1α,2α-methylene-5α-cholestan-3-one (German Pat. No. 1,183,500) are reacted in twenty Erlenmeyer flasks with a Mycobacterium spec. NRRL-B-3805 culture and then worked up, thus obtaining 1α,2α-methylene-5α-androstane-3,17-dione.

(B) Examples Concerning the Chemical Further Processing of the Androstane-3,17-dione Derivatives

EXAMPLE 1

7.2 g. of 1α-methyl-5α-androstane-3,17-dione dissolved in 150 ml. of absolute methanol is combined with 100 mg. of p-toluenesulfonic acid and refluxed for 20 minutes. The solution is cooled and combined with 5 ml. of 10% sodium hydroxide solution and thereafter reduced at 0° C. by adding 1 g. of finely pulverized sodium borohydride in incremental portions. After this addition (20 minutes), the mixture is agitated for 2 hours with ice cooling and then combined with 50 ml. of 1N sulfuric acid and refluxed for one hour. The suspension is then stirred into 300 ml. of ice-water-sodium chloride. The thus-precipitated product is vacuum-filtered, dried at 50° C. under vacuum, and recrystallized from diisopropyl ether, thus obtaining 4.15 g. of 17β-hydroxy-1α-methyl-5α-androstan-3-one, m.p. 203°–205° C., which has a pronounced androgenic activity (German Pat. No. 1,152,100).

EXAMPLE 2

Under the conditions of Example 1, 2.8 g. of 1α,2α-methylene-5α-androstane-3,17-dione is reduced with sodium borohydride. After the reaction mixture has been worked up, the yield is 1.3 g. of 17β-hydroxy-1α,-2α-methylene-5α-androstan-3-one (German Pat. No. 1,183,500).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of an androstane-3,17-dione compound of the formula

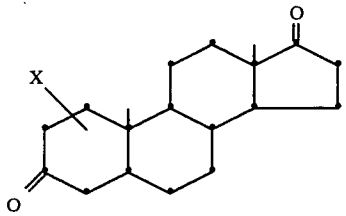

wherein X is 1,2-methylene or 1- or 2-methyl, comprising fermenting; in the absence of 4 androstene-3,17-dione degradation inhibitors, a sterol of the formula

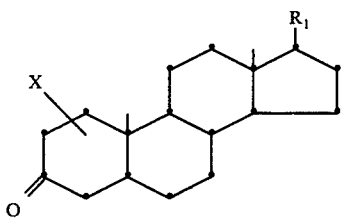

wherein X is as above and $R_1$ is a saturated or unsaturated hydrocarbon sterol side chain of 8–10 carbon atoms with a micro-organism culture capable of degrading the sterol side chain.

2. The process of claim 1, comprising the further step of either (a) selectively reducing the 17-keto group of the thus-produced androstane-3,17-dione or (b) selectively reacting the 17-keto group of the thus-produced androstane-3,17-dione with an organometallic compound of the formula MeR$_4$ wherein R$_4$ is alkyl, alkenyl or alkynyl of up to 4 carbon atoms and Me is an alkali metal atom or a magnesium halide residue, to produce a 17β-hydroxyandrostan-3-one compound of the formula

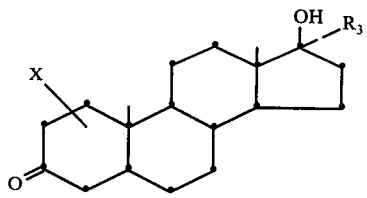

wherein X is 1,2-methylene or 1- or 2-methyl and R$_3$ is hydrogen or R$_4$, respectively.

3. The process of claim 2, comprising the additional steps of ketalizing the carbonyl at the 3-position of the androstane-3,17-dione compound prior to the selective reduction or selective reaction and subsequently cleaving the ketal at the 3-position of the 17β-hydroxyandrostan-3-one compound after the selective reduction or selective reaction.

4. The process of claim 2, wherein R$_3$ is hydrogen, methyl, ethyl, vinyl or ethinyl.

5. The process of claim 1, wherein the microorganism culture is of the genera Arthrobacter, Brevibacterium, Microbacterium, Protaminobacter, Bacillus, Norcardia or Streptomyces.

6. The process of claim 1, wherein the microorganism culture is of the genus Mycobacterium.

7. The process of claim 1, wherein the microorganism culture is Mycobacterium spec. NRRL-B-3805.

8. The process of claim 2, wherein the microorganism culture is of the genera Arthrobacter, Brevibacterium, Microbacterium, Protaminobacter, Bacillus, Norcarida or Streptomyces.

9. The process of claim 2, wherein the microorganism culture is of the genus Mycobacterium.

10. The process of claim 2, wherein the microorganism culture is Mycobacterium spec. NRRL-B-3805.

* * * * *